(12) United States Patent
Hollender et al.

(10) Patent No.: US 10,194,889 B2
(45) Date of Patent: Feb. 5, 2019

(54) METHODS, SYSTEMS AND COMPUTER PROGRAM PRODUCTS FOR MULTI-RESOLUTION IMAGING AND ANALYSIS

(71) Applicant: Duke University, Durham, NC (US)

(72) Inventors: Peter J. Hollender, Durham, NC (US); Nicholas B. Bottenus, Durham, NC (US)

(73) Assignee: Duke University, Durham, NC (US)

( * ) Notice: Subject to any disclaimer, the term of this patent is extended or adjusted under 35 U.S.C. 154(b) by 157 days.

(21) Appl. No.: 14/259,875

(22) Filed: Apr. 23, 2014

(65) Prior Publication Data

US 2015/0305717 A1   Oct. 29, 2015

(51) Int. Cl.
| | |
|---|---|
| *A61B 8/08* | (2006.01) |
| *G01N 29/07* | (2006.01) |
| *G01N 29/09* | (2006.01) |
| *A61B 8/00* | (2006.01) |
| *A61B 8/12* | (2006.01) |
| *G01N 29/06* | (2006.01) |
| *G01S 7/52* | (2006.01) |

(52) U.S. Cl.
CPC ............... *A61B 8/485* (2013.01); *A61B 8/12* (2013.01); *A61B 8/4494* (2013.01); *A61B 8/5223* (2013.01); *G01N 29/0654* (2013.01); *G01N 29/07* (2013.01); *G01N 29/09* (2013.01); *G01S 7/52022* (2013.01); *G01S 7/52036* (2013.01); *G01N 2291/011* (2013.01); *G01N 2291/018* (2013.01); *G01N 2291/02827* (2013.01); *G01N 2291/044* (2013.01); *G01N 2291/0422* (2013.01); *G01N 2291/106* (2013.01)

(58) Field of Classification Search
CPC ......... A61B 8/485; A61B 8/12; A61B 8/4494; A61B 8/5223; G01N 29/0654; G01N 29/07; G01N 29/09; G01S 7/52022; G01S 7/52036
See application file for complete search history.

(56) References Cited

U.S. PATENT DOCUMENTS 6,014,473 A * 1/2000 Hossack ............... A61B 8/145
                                                     348/169
6,309,356 B1 * 10/2001 Ustuner ............... G01S 7/52026
                                                     600/443
(Continued)

OTHER PUBLICATIONS

Song et al., "Comb-push Ultrasound Shear Elastography (CUSE): A Novel Method for Two-dimensional Shear Elasticity Imaging of Soft Tissues", IEEE Trans Med Imaging. Sep. 2012 ; 31(9): 1821-1832.*

*Primary Examiner* — Tse Chen
*Assistant Examiner* — Joanne Hoffman
(74) *Attorney, Agent, or Firm* — Myers Bigel, P.A.

(57) ABSTRACT

Methods for determining a mechanical parameter for a sample having a target region include generating a tissue displacement in the target region; transmitting tracking pulses in the target region; receiving corresponding echo signals for the tracking pulses in the target region at a plurality of positions; analyzing the echo signals at one or more multi-resolution pairs of the positions and/or acquisition times; and determining at least one mechanical parameter of the target region based on the echo signals at the one or more multi-resolution pairs of positions and/or acquisition times.

14 Claims, 11 Drawing Sheets

(56) References Cited

U.S. PATENT DOCUMENTS

| | | | |
|---|---|---|---|
| 6,371,912 B1* | 4/2002 | Nightingale | A61B 5/0053 600/437 |
| 6,764,448 B2 | 7/2004 | Trahey et al. | |
| 6,951,544 B2 | 10/2005 | Trahey et al. | |
| 7,892,188 B2* | 2/2011 | Walker | A61B 5/0048 600/368 |
| 8,118,744 B2 | 2/2012 | Palmeri et al. | |
| 2001/0036302 A1* | 11/2001 | Miller | G06T 3/0068 382/128 |
| 2004/0059220 A1* | 3/2004 | Mourad | A61B 5/0048 600/442 |
| 2005/0165306 A1* | 7/2005 | Zheng | A61B 8/00 600/437 |
| 2006/0051734 A1* | 3/2006 | McNeill | A61B 5/0051 435/4 |
| 2006/0052699 A1* | 3/2006 | Angelsen | A61B 8/14 600/437 |
| 2008/0249419 A1* | 10/2008 | Sekins | A61B 8/08 600/463 |
| 2009/0304246 A1* | 12/2009 | Walker | G01S 7/52034 382/128 |
| 2010/0016718 A1* | 1/2010 | Fan | A61B 8/00 600/438 |
| 2010/0069751 A1* | 3/2010 | Hazard | A61B 5/415 600/438 |
| 2010/0280373 A1* | 11/2010 | Fan | A61B 8/0833 600/439 |
| 2010/0286516 A1* | 11/2010 | Fan | A61B 8/08 600/438 |
| 2012/0236689 A1* | 9/2012 | Brown | B06B 1/0637 367/118 |

\* cited by examiner

METHODS, SYSTEMS AND COMPUTER PROGRAM PRODUCTS FOR MULTI-RESOLUTION IMAGING AND ANALYSIS

STATEMENT OF GOVERNMENT SUPPORT

This invention was made with government support under Grant No R37HL096023 awarded by the National Institutes of Health. The government has certain rights in the invention.

FIELD OF THE INVENTION

The present invention relates to ultrasound imaging and analysis, and in particular, to determining mechanical parameters of a sample using multi-resolution shear wave and/or axial displacement imaging and analysis.

BACKGROUND

Acoustic Radiation Force (ARF) shear wave elasticity imaging methods typically use a transverse propagation velocity of mechanical shear waves in materials to estimate mechanical properties of a sample, such as material elasticity constants. These techniques may be adapted into imaging systems to compute the local shear wave propagation velocity as a function of both axial and lateral position. The velocity may be calculated by estimating the differences in arrival times of the shear waves, either at different recording locations or from different excitation locations.

The velocity of the shear wave may, therefore, be estimated over a predefined lateral kernel or distance. If the kernel is relatively small, the arrival time difference will also be small, and therefore, small errors in the arrival time may result in large errors in the estimate. Larger kernels are more resistant to small arrival time errors, but may result in a loss of resolution or lateral blurring of the image.

SUMMARY OF EMBODIMENTS OF THE INVENTION

In some embodiments, methods for determining a mechanical parameter for a sample having a target region include generating a tissue displacement in the target region; transmitting tracking pulses in the target region; receiving corresponding echo signals for the tracking pulses in the target region at a plurality of positions; analyzing the echo signals at one or more multi-resolution pairs of the positions and/or acquisition times; and determining at least one mechanical parameter of the target region based on the echo signals at the one or more multi-resolution pairs of the positions and/or acquisition times.

In some embodiments, one or more multi-resolution pairs of positions that are spatially-related are selected. The spatially-related pairs of positions may include a first set of positions having a first resolution therebetween and a second set of positions having a second resolution therebetween that is different from the first resolution. The first set of positions and the second set of positions may be spatially equivalent such that a sum of distances for the first set of positions is equivalent to a sum of distances for the second set of positions. Analyzing echo signals at one or more multi-resolution pairs of positions may include determining a time-of-flight and/or velocity of a shear wave. A time-of-flight difference and/or velocity estimate of the shear wave for the first and second set of spatially equivalent positions may be averaged.

In some embodiments, the plurality of positions comprise positions of ultrasound array elements that transmit the tracking pulses and receive the echo signals and/or positions of ultrasound array elements that transmit an excitation pulse configured to cause the tissue displacement. In some embodiments, analyzing echo signals at one or more multi-resolution pairs of positions includes combining echo signals at the one or more pairs of related positions.

In some embodiments, the at least one mechanical parameter includes at least one of shear elasticity modulus, Young's modulus, dynamic shear viscosity, shear wave velocity and mechanical impedance of the sample.

In some embodiments, the sample is an in vivo human tissue sample.

In some embodiments, the tissue displacement are detected with an internally inserted ultrasound probe array. In some embodiments, the shear waves are detected with an externally applied ultrasound array.

In some embodiments, the applied shear wave source is an ultrasound transducer and/or mechanical vibrator.

In some embodiments, an ultrasound system for determining a mechanical parameter for a sample having target region includes an ultrasound transducer array. A controller is configured to control the ultrasound transducer to generate a tissue displacement in the target region, to transmit tracking pulses in the target region, and to receive corresponding echo signals for the tracking pulses in the target region at a plurality of positions. A signal analyzer is configured to analyze the echo signals at one or more multi-resolution pairs of the positions and/or acquisition times and to determine at least one mechanical parameter of the target region based on the echo signals at the one or more multi-resolution pairs of the positions and/or acquisition times.

In some embodiments, a computer program product for determining a mechanical parameter for a sample having a target region includes a non-transient computer readable medium having computer readable program code embodied therein. The computer readable program code includes computer readable program code configured to generate a tissue displacement in the target region with an ultrasound transducer array; computer readable program code configured to transmit tracking pulses in the target region with the ultrasound transducer array; computer readable program code configured to receive corresponding echo signals for the tracking pulses in the target region at a plurality of positions with the ultrasound transducer array; computer readable program code configured to analyze the echo signals at one or more multi-resolution pairs of the positions and/or acquisition times; and computer readable program code configured to determine at least one mechanical parameter of the target region based on the echo signals at the one or more multi-resolution pairs of the positions and/or acquisition times.

BRIEF DESCRIPTION OF THE DRAWINGS

The accompanying drawings, which are incorporated in and constitute a part of the specification, illustrate embodiments of the invention and, together with the description, serve to explain principles of the invention.

DETAILED DESCRIPTION OF EMBODIMENTS OF THE INVENTION

Figure 1:
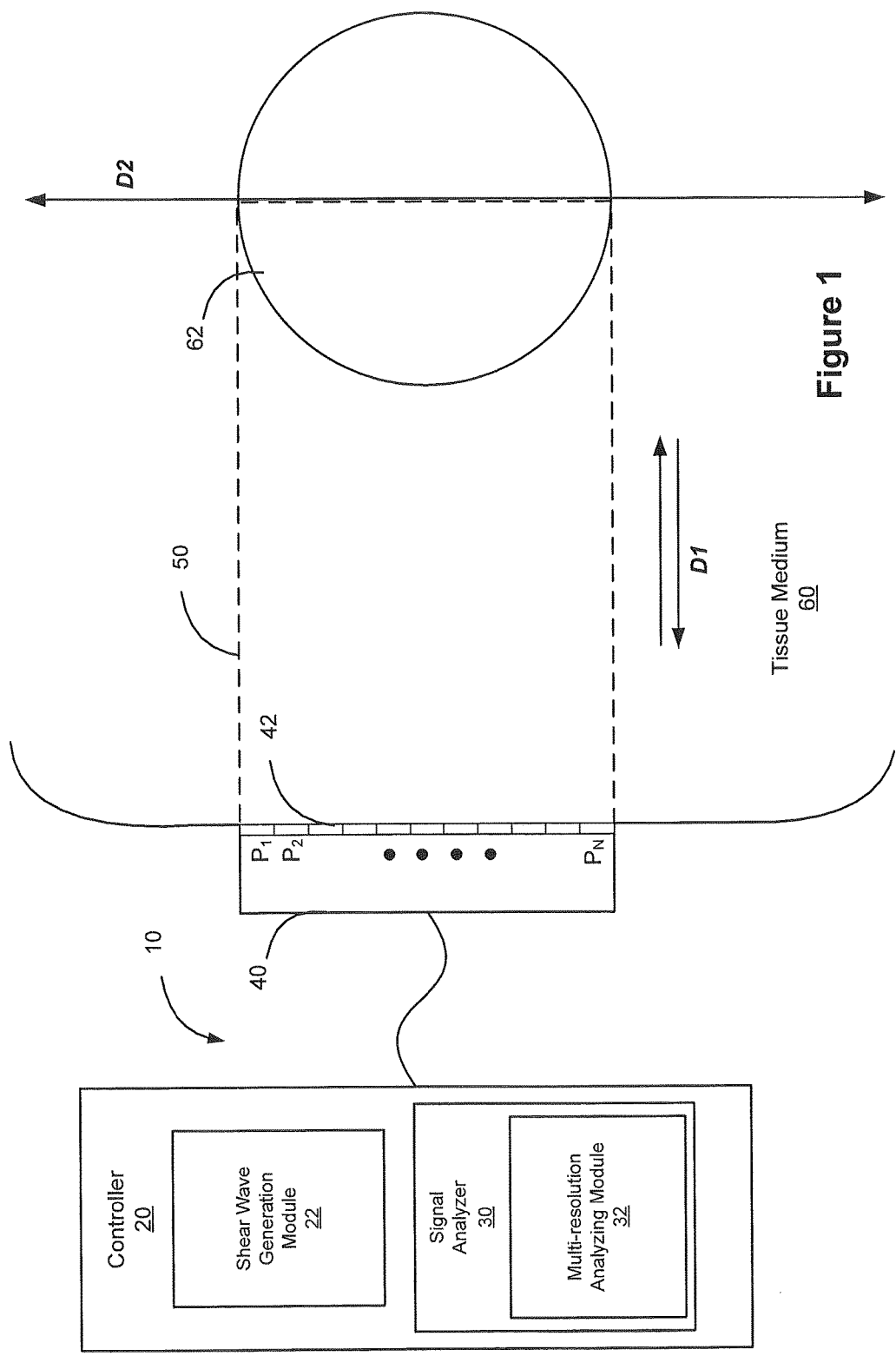
FIG. 1 is a schematic diagram of ultrasound systems, methods and computer program products according to some embodiments.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. For example, the term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

The present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, the present invention may be embodied in hardware and/or in software (including firmware, resident software, micro-code, etc.). Furthermore, embodiments of the present invention may take the form of a computer program product on a computer-usable or computer-readable non-transient storage medium having computer-usable or computer-readable program code embodied in the medium for use by or in connection with an instruction execution system.

The computer-usable or computer-readable medium may be, for example but not limited to, an electronic, optical, electromagnetic, infrared, or semiconductor system, apparatus, or device. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM).

Embodiments according to the present invention are described herein with reference to the term "tissue." It will be understood that the term tissue can include biological materials, such as, blood, organs, vessels, and other biological objects found in a body. It will be further understood that embodiments according to the present invention may be applicable to humans as well as other species. Embodiments according to the present invention may also be utilized to image objects other than tissue.

It will be understood that the scope of the present invention includes, for example, two dimensional (2D) ultrasound imaging and 3D (or volumetric) ultrasound imaging. In addition, the components of the ultrasound imaging described herein may be packaged as a single unit or packaged separately and interconnected to provide the functions described herein.

Embodiments according to the present invention are also described by reference to Acoustic Radiation Force Imaging (ARFI) which is described in greater detail, for example, in U.S. Pat. No. 6,371,912, the entire disclosure of which is incorporated herein by reference. An acoustic radiation force may be used to apply a force to tissue thereby causing the tissue to move in the direction of the force and/or to generate a shear wave.

As used herein, a "shear wave" is a form of sample displacement in which a shear wave source, such as ultrasound energy, is transmitted into the sample in one direction and generates an extended shear wave the propagates in another direction that is substantially orthogonal to the direction of the shear wave source. The displacement caused by a shear wave source may be in a range between about 0.1 µm and about 300 µm. Other displacements can be provided.

The term "time of arrival" refers herein to the measured elapsed time between the transmission of a transmitting signal and the return of a corresponding reflected signal. The time of arrival is measured by conventional measurement techniques.

The term "multi-resolution" refers to measurements made with different resolutions. For example, multi-resolution measurements may include ultrasound measurements having different resolution characteristics, such as ultrasound echo signals from different transmit and receive locations. The transmit/receive locations may be defined by ultrasound array element positions and/or electronic steering and focusing of the ultrasound array. An example of a multi-resolution measurement includes ultrasound echo signals received at closely-spaced ultrasound array elements, which have a relatively high resolution, and ultrasound echo signals received at ultrasound array elements that have a relatively greater spacing, which have a lower resolution.

As illustrated in FIG. 1, an ultrasound system 10 includes a controller 20, a signal analyzer 30 and an ultrasound transducer array 40. The ultrasound transducer array 40 may include a plurality of array elements 42 at positions $P_1$ through $P_N$. The array elements 42 are configured to transmit and receive ultrasound signals 50, and may be contacted to a target medium such as a tissue medium 60. As illustrated, the tissue medium 60 includes a target region 62. As illustrated, the ultrasound array 40 may include ultrasound array elements 42 that define transmit/receive locations for transmitting and receiving ultrasound signals along a direction D1. In some embodiments, the array 40 may be configured to transmit sufficient ultrasound energy, for example, by applying an impulse excitation acoustic radiation force to the medium 60, to generate a shear wave that propagates in a direction D2 that is orthogonal to D1. The array 40 may also be configured to interrogate the tissue medium 60, for example, using ARFI or B-mode imaging techniques to monitor the tissue through time before and/or after the shear wave excitation force has been applied. ARFI imaging is discussed in U.S. Pat. Nos. 6,371,912; 6,951,544 and 6,764,448, the disclosures of which are hereby incorporated by reference in their entireties. Shear waves are discussed in U.S. Pat. Nos. 8,118,744 and 6,764,448, the disclosures of which are hereby incorporated by reference in their entireties. The ultrasound transducer array 40 may be a one-dimensional array configured to generate two-dimensional images or the ultrasound transducer array 40 may be a two-dimensional array configured to generate three-dimensional images.

The controller 20 may include a shear wave generation module 22 and the signal analyzer 30 may include a multi-resolution analyzing module 32. The shear wave generation module 22 and the multi-resolution analyzing module 32 may be configured to control the array 40 and/or to analyze echo signals received by the array 40 as described herein. The shear wave generation module 22 and the multi-resolution analyzing module 32 may include hardware, such as control and/or analyzing circuits, and/or software stored on a non-transient computer readable medium for carrying out operations described herein.

Figure 3:
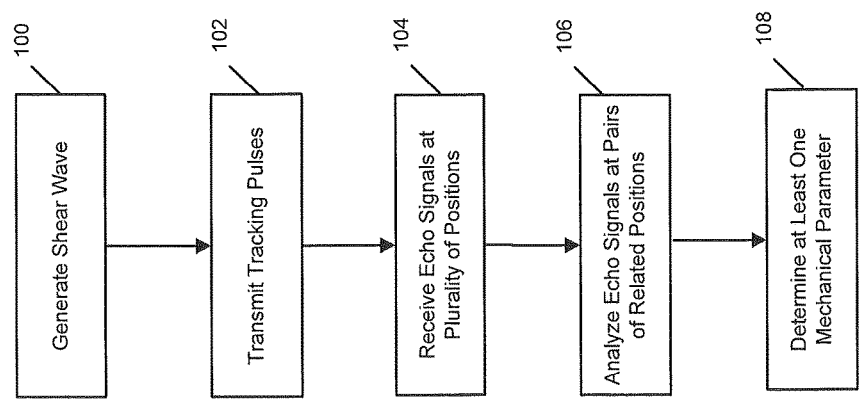
FIG. 3 is a flowchart illustrating operations according to some embodiments.

As illustrated in FIGS. 1 and 3, the shear wave generation module 22 may provide control signals to cause the array 40 to generate a shear wave in the target region 62 (Block 100), to transmit tracking pulses in the target region 62 (Block 102) and to receive corresponding echo signals for the tracking pulses in the target region 62 at a plurality of positions (Block 104). The multi-resolution analyzing module 32 analyzes the echo signals at one or more multi-resolution pairs of the positions and/or acquisition times (Block 106) and determines at least one mechanical parameter of the target region 62 based on the echo signals at the one or more multi-resolution pairs of positions and/or acquisition times (Block 108). The mechanical parameter may include a shear elasticity modulus, Young's modulus, dynamic shear viscosity, shear wave velocity and/or mechanical impedance of the sample. The multi-resolution analyzing module 32 may be configured to provide an ultrasound image based on the received ultrasound signals and/or the calculated mechanical parameters.

Figure 2:
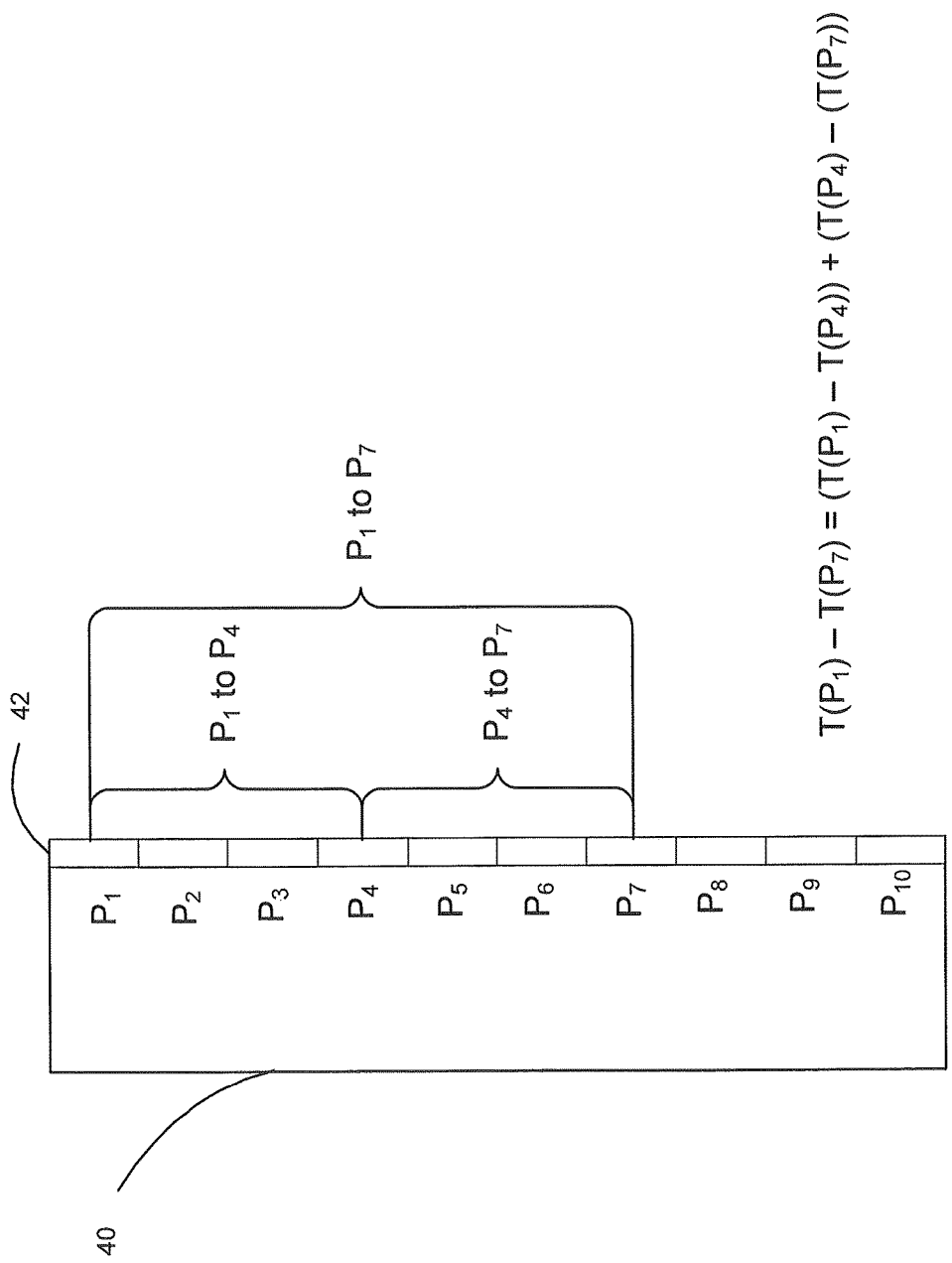
FIG. 2 is a schematic diagram of an ultrasound array according to some embodiments.

FIG. 2 illustrates an example array 40 with array elements 42 at positions $P_1$ to $P_{10}$. As shown in FIG. 2, sets of pairs of related positions that are spatially related, such as multi-resolution pairs of positions, may be selected. For example, a difference between the first position $P_1$ and the seventh position $P_7$ is equivalent to the difference between the first position $P_1$ and the fourth position $P_4$ combined or summed with the difference between the fourth position $P_4$ and the seventh position $P_7$. The spatially related pairs of positions shown in FIG. 2 have different resolution characteristics due to the different distances between the array element positions. For example, the resolution of ultrasound data between the first position $P_1$ and the seventh position $P_7$ is generally less clearly resolved and has less noise than the resolution and noise of data between positions that are more closely spaced, such as between the first position $P_1$ and the fourth position $P_4$ or the first position $P_4$ and the seventh position $P_7$. However, the distance between the first position $P_1$ and the seventh position $P_7$ is equivalent to the distance between the first position $P_1$ and the fourth position $P_4$ combined or added to the distance between the first position $P_4$ and the seventh position $P_7$. Accordingly, the time-of-flight measurements for a shear wave generated in the sample medium will generally satisfy the following conditions: $T(P_1)-T(P_7)=(T(P_1)-T(P_4))+(T(P_4)-T(P_7))$, where $T(P_n)$ is the time-of-flight measurement at a given element position. It should be understood that various sets of element positions may be selected, for example, so that a sum of distances for one set of element positions is equivalent to a sum of distances for another set of positions. Time-of-flight measurements may be used to track the position of shear waves through time and/or correlate their space/time coordinates to estimate shear wave speeds. The time-of-flight measurements may track any suitable characteristic of the shear wave, including a time of peak displacement, shear wave leading edge, shear wave trailing edge and the like. Although time-of-flight measurements may be used to track the shear wave, it should be understood that any suitable parameter may be used to estimate a time delay between the signals at one or more pairs of points, including, but not limited to, normalized cross-correlation, cross-correlation and/or a sum-of-absolute-difference method. In some embodiments, the parameter, such as shear wave time-of-flight and/or velocity data, is averaged for two or more sets of spatially equivalent positions.

In some embodiments, the echo signals at one or more pairs of related positions may be combined by summing and/or subtracting. In some embodiments, the echo signals at one or more pairs of related positions may be combined using delay-and-sum beamforming.

In some embodiments, the shear wave and/or displacement data acquired as described herein can be used to quantify the stiffness of tissues and/or organs, which may be useful in the clinical setting to track the progression of disease and to monitor the response of diseased tissues to treatments (e.g., drug regimens, diet/lifestyle changes, chemotherapy, and radiotherapy). The techniques described herein can be used to characterize the stiffness of biological tissues using their dynamic displacement response to impulsive acoustic radiation force excitations. This may allow for absolute and relative quantification of tissue stiffness to aid in clinical treatment of a variety of pathologic conditions, such as liver disease (e.g., liver steatosis, liver fibrosis and cirrhosis), atherosclerosis, benign prostatic hypertrophy (BPH), muscular dystrophy, products of ablation, cancer in various organs/tissue, thyroid disease and/or skin diseases. Accordingly, the tissue sample may be an in vivo human tissue sample. The shear waves can be detected and/or generated using an internally inserted ultrasound probe array (such as an ultrasound probe array configured for insertion into an orifice of the body) or with an externally applied ultrasound array.

The mechanical parameter(s) of the sample can be correlated to measurement of healthy/diseased tissue states, such as by using actual clinical data and known healthy/diseased tissue states. The clinical data can be based on other factors such as demographic information, e.g., age, gender and race, to correlate the measurement of the mechanical parameter(s) with a measurement of healthy/diseased tissue states in a particular demographic group.

In some embodiments, the mechanical parameter(s) of the sample can be monitored as a function of time by performing the multi-resolution analyzing techniques on a sample repeatedly over a period of time. A healthy/diseased tissue state determination can be based on a change in the mechanical parameter(s) as a function of time. For example, the mechanical parameter(s) can be monitored over a period of minutes, hours, days, weeks, months or even years to determine the progression of the disease and/or the efficacy of treatment.

In some embodiments, the mechanical parameter(s) may be used to form an ultrasound image, such as a B-mode image or an ARFI image.

Although embodiments according to the invention are described herein with respect to shear waves, it should be understood that multi-resolution analysis may be used to estimate other forms of tissue motion and/or displacement, including axial tissue motion (e.g., using radio frequency (RF) traces instead of a motion profile). Moreover, although embodiments are described with respect to spatially offset multi-resolution values, temporally offset values may be used, for example, to estimate the motion/displacement of a sample over time.

Embodiments according to the invention will now be described with respect to the following non-limiting examples.

Time-of-Flight Estimation

For any pair of recording locations away from a single source in a homogenous medium, the signals of tissue motion at each location are scaled, time-delayed versions of one another, with the time delay reflecting the shear wave velocity between the recording locations as follows:

$$u(x_j, t) = \left(\frac{x_i}{x_j}\right) u\left(x_i, t - \left(\frac{x_j - x_i}{c}\right)\right) \quad (1)$$

For any pair of source excitations, the tissue motion signals recorded at any single location outside of the sources will be time-delayed versions of one another with the time delay reflecting the shear wave velocity between the locations. In a heterogeneous medium, c becomes c(x), so equation (1) may be written as follows:

$$u(x_j, t) = \left(\frac{x_i}{x_j}\right) u\left(x_i, t - \left(\int_{x_i}^{x_j} \frac{1}{c(x)} dx\right)\right) \quad (2)$$

This assumes that the derivative of c(x) is small relative to the wavelength such that there is negligible reflection. In the case of a single, significant reflection, u(x,t) may be split into its transmitted and reflected components $u_T(x,t)$ and $u_R(x,t)$, which are scaled by transmission and reflection coefficients, respectively. For multiple reflections, additional wave components may be added. In practice, a directional filter may be used to suppress the reflected wave components in post-processing, and most time delay estimators are robust to variations in signal amplitude. Various techniques may be used to estimate the time delay between the two signals, including the sum-of-absolute differences, normalized cross-correlation, and phase-based methods.

For M discrete ultrasound element receiver locations, there are $M^2$ possible sets of time delay pairs. In this example, it is assumed that all M receivers are located collinearly along the direction of wave propagation and that the source of the wave is outside of the receiver positions. To form a consistent set, the delays obey a set of rules:

1) $\Delta t_{ii}=0$. A signal compared with itself will indicate no time delay.
2) $\Delta t_{ij} \Delta t_{ji}$. The delay is the same regardless of which signal is the reference.
3) $\Delta t_{ij}+\Delta t_{jk}=\Delta t_{ik}$. The delay between any two points is independent of the path of delays between the points.

In this formulation, there are M−1 degrees of freedom, and the time delays in single-subscript notation are $\Delta t_i = \Delta t_{i(i+1)}$, which are each the denominator term for the corresponding local shear wave velocity, $$c_i = \Delta x_i / \Delta t_i = \frac{1}{\int_{x_i}^{x_i+1} \frac{1}{c(x)} dx}, \quad (3)$$

with $\Delta x_i = \Delta x_{i(i+1)}$. To take advantage of multiple estimates, each of the observations $\Delta t_{ij}$ is expressed as the linear combination of the parameters $\Delta t_i$, that is:

$$\Delta t_{ij} = \sum_{k=i}^{j-1} \Delta t_{kk+1}, \text{ for } j > i, \text{ and} \quad (4)$$

$$\Delta t_{ij} = \sum_{k=j+1}^{i} \Delta t_{kk-1} \text{ for } j < i. \quad (5)$$

Expressed in matrix form as $A\vec{b}=\vec{y}$, with $\vec{b}=\Delta T$ and $\vec{y}=\Delta t$, $$\begin{bmatrix} 1 & 0 & 0 & \ldots & 0 \\ 1 & 1 & 0 & \ldots & 0 \\ \ldots & & & & \\ 1 & 1 & 1 & \ldots & 1 \\ 0 & 1 & 0 & \ldots & 0 \\ \ldots & & & & \\ 0 & 0 & \ldots & 0 & 1 \end{bmatrix} \begin{bmatrix} \Delta T_1 \\ \Delta |T_2 \\ \Delta T_3 \\ \ldots \\ \Delta T_{M-2} \\ \Delta T_{M-1} \end{bmatrix} = \begin{bmatrix} \Delta t_{12} \\ \Delta t_{13} \\ \ldots \\ \Delta t_{1M} \\ \Delta t_{23} \\ \ldots \\ \Delta t_{M-1M} \end{bmatrix} \quad (6)$$

The above may be converted to a classical inverse problem, and to recover $\Delta T$, the Least-Squares solution may be used as follows:

$$\vec{b} = (A^T A)^{-1} A^T \vec{y} \quad (7)$$

Notably, the Least-Squares solution may be expressed as a linear transformation of the observations, and the matrix inversion step may be performed a priori on the condition matrix A. Because A is relatively simple in structure, $(A^T A)^{-1} A^T$ may be examined to consider a solution. For example, a case where there are three receive locations having three observations, $\Delta t_{12}$, $\Delta t_{23}$, and $\Delta t_{13}$ may be considered as follows:

$$\begin{bmatrix} 1 & 0 \\ 0 & 1 \\ 1 & 1 \end{bmatrix} \begin{bmatrix} \Delta T_{12} \\ \Delta T_{23} \end{bmatrix} = \begin{bmatrix} \Delta t_{12} \\ \Delta t_{23} \\ \Delta t_{13} \end{bmatrix} \quad (8)$$

The solution for the high resolution estimates $\Delta T_{12}$ and $\Delta T_{12}$ may be expressed as follows:

$$\Delta T_{12} = \frac{2}{3}(\Delta t_{12}) + \frac{1}{3}(\Delta t_{13} - \Delta t_{23}) \quad (9)$$

$$\Delta T_{23} = \frac{2}{3}(\Delta t_{23}) + \frac{1}{3}(\Delta t_{13} - \Delta t_{12}) \quad (10)$$

Figure 4:
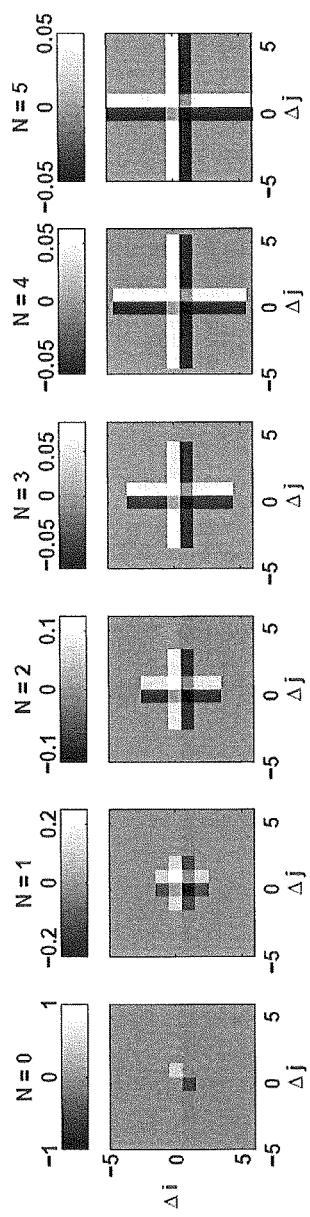
FIG. 4 is a series of images illustrating a Least-Squares solution for a resolution estimate expressed as a filter applied to neighboring multi-resolution observations according to some embodiments.

Accordingly, there is a direct observation of the estimate in addition to two other measurements, whose difference should be equal to the first direct observation. In some embodiments, the direct observation is preferentially weighted. Expanding this concept to find a high resolution estimate from all multi-resolution estimates within N samples of the estimate, a pattern emerges in the linear combination applied to the nearby observations (e.g., the row of $(A^T A)^{-1} A^T$ corresponding to the estimate). FIG. 4 illustrates the coefficients applied to the neighboring observations to estimate $\Delta T_{ij}$, for different neighborhood sizes, shown as a filter that can be applied to the main diagonal of a matrix containing all observations $\Delta t_{ij}$.

Figure 5:
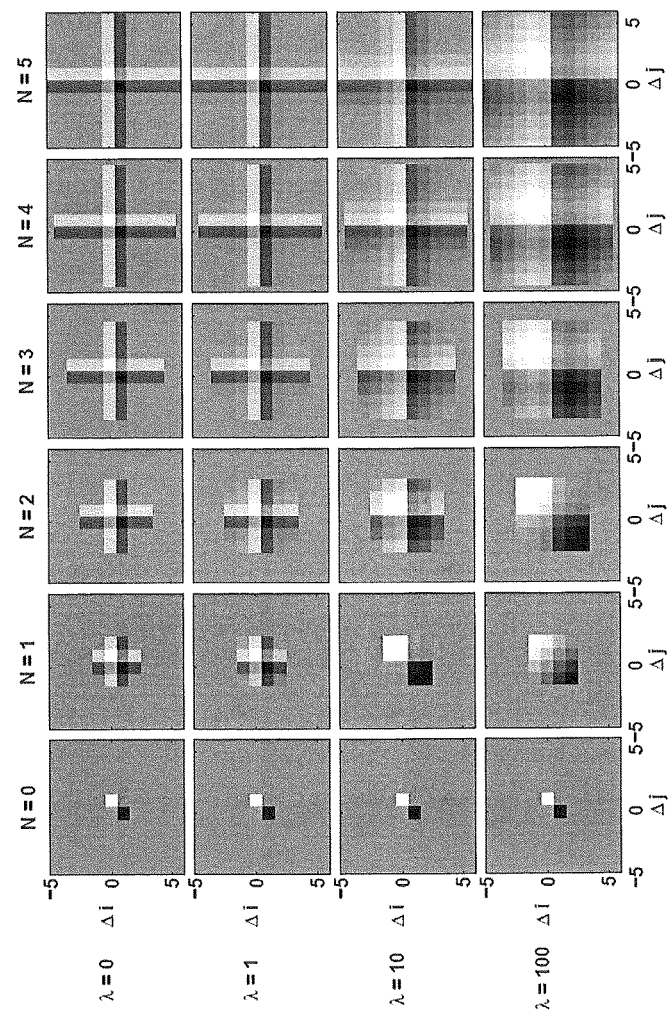
FIG. 5 is a series of images illustrating a Least-Squares solution for a high resolution estimate expressed as a filter applied to neighboring multi-resolution observations and including varying degrees of first-order Tikhonov regularization according to some embodiments.

With no multi-resolution kernel (N=0), the estimate is simply the average of the forward and reverse estimates $\Delta t_{ij}$ and $-1*\Delta_{ji}$, which, for cross-correlation, are the same. The progressive time-delays are estimated in this case. For larger multi-resolution kernels, however, the solutions may include all of the two-observation multipath combinations that yield the estimate within N samples. From this formulation, the concept of spatial regularization may be introduced to favor solutions that are more smooth. For example, using Tikhonov Regularization, the solution may be expressed as follows:

$$\vec{b} = (A^T A + \lambda \Gamma^T \Gamma)^{-1} A^T \vec{y} \qquad (11)$$

where $\Gamma$ is a regularization matrix, scaled by the regularization factor $\lambda$. To favor solutions with small first derivatives, the difference operator is chosen for $\Gamma$. As $\lambda$ is increased, solutions are favored that are increasingly smooth. This may be seen in the character of the filter representation shown in FIG. 5.

Finite Element Method Simulation

A finite element method (FEM) simulation of a shear wave generated by acoustic radiation force was created using LS-DYNA (Livermore Software Technology Corporation (Livermore, Calif., USA)). A Siemens Acuson ER7B linear array transducer (Siemens Healthcare Solutions (Malvern, Pa., USA)) was simulated for excitation, with a transmit focus of 15 mm at F/3. The induced shear wave was recorded at 1,000 frames per second with a lateral spacing of 0.1 mm over 6 mm to the right of the excitation. The elastic material was simulated with a Young's modulus of 4.5 kPa on the left side, and 24 kPa on the right side, with a vertical layer boundary 3 mm to the right of the excitation. The displacements calculated from the FEM simulation were used without simulated ultrasonic tracking.

Figure 6:
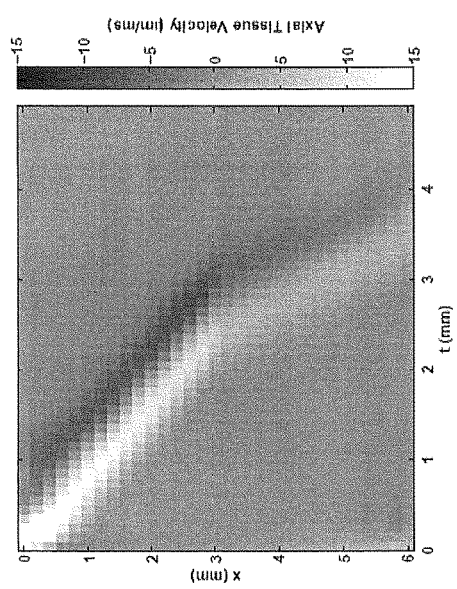
FIG. 6 is an image of an axial tissue velocity as a function of lateral position for a shear wave generated at x=0 and tracked as it propagates from left to right and encountering a boundary at x=3 according to some embodiments.

FIG. 6 illustrates the axial tissue velocity at the focal depth for a wave generated on the left side of the region of interest (ROI) (x=0 mm), and propagating to the right, encountering the boundary at x=3 mm. A directional filter has been applied to the data to remove the reflected wave. The change in shear wave velocity is apparent in the slope of the wave.

Figure 7A:
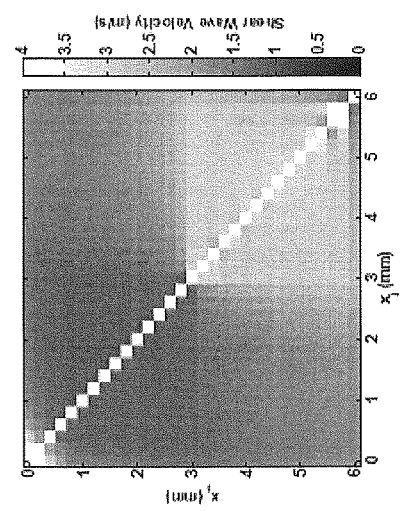
FIG. 7a is an image illustrating combinations of time delay estimates for a wave excited at x=0 mm and propagating across a boundary at x=3 mm according to some embodiments.
Figure 7B:
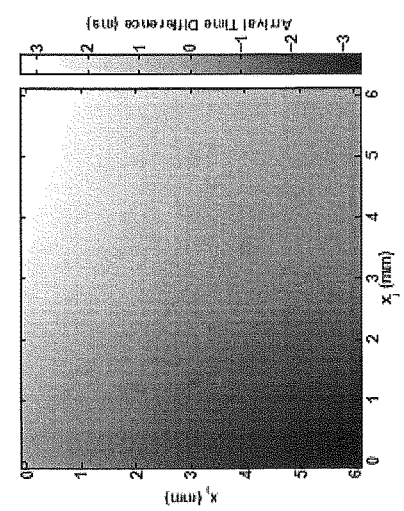
FIG. 7b is an image of the data of FIG. 7a which has been converted to velocity estimates according to some embodiments.

FIG. 7a illustrates all of the estimated time delays for each pair of receive locations at the focal depth. FIG. 7b illustrates a conversion of the time delays of FIG. 7a to velocity estimates. There is a vertical boundary at x=3 mm. The main diagonal ($x_i=x_j$) has time delays that are identically zero, while those in the upper right ($x_j>x_i$) are positive and those in the lower left ($x_j<x_i$) are negative. In both directions, the time delay scales with $|(x_j-x_i)|$. As the pair of tracking locations gets farther apart, $|(x_j-x_i)|$ gets larger, as does the measured time delay. The degradation in resolution is apparent away from the main diagonal as the layer boundary becomes blurred.

Figure 8:
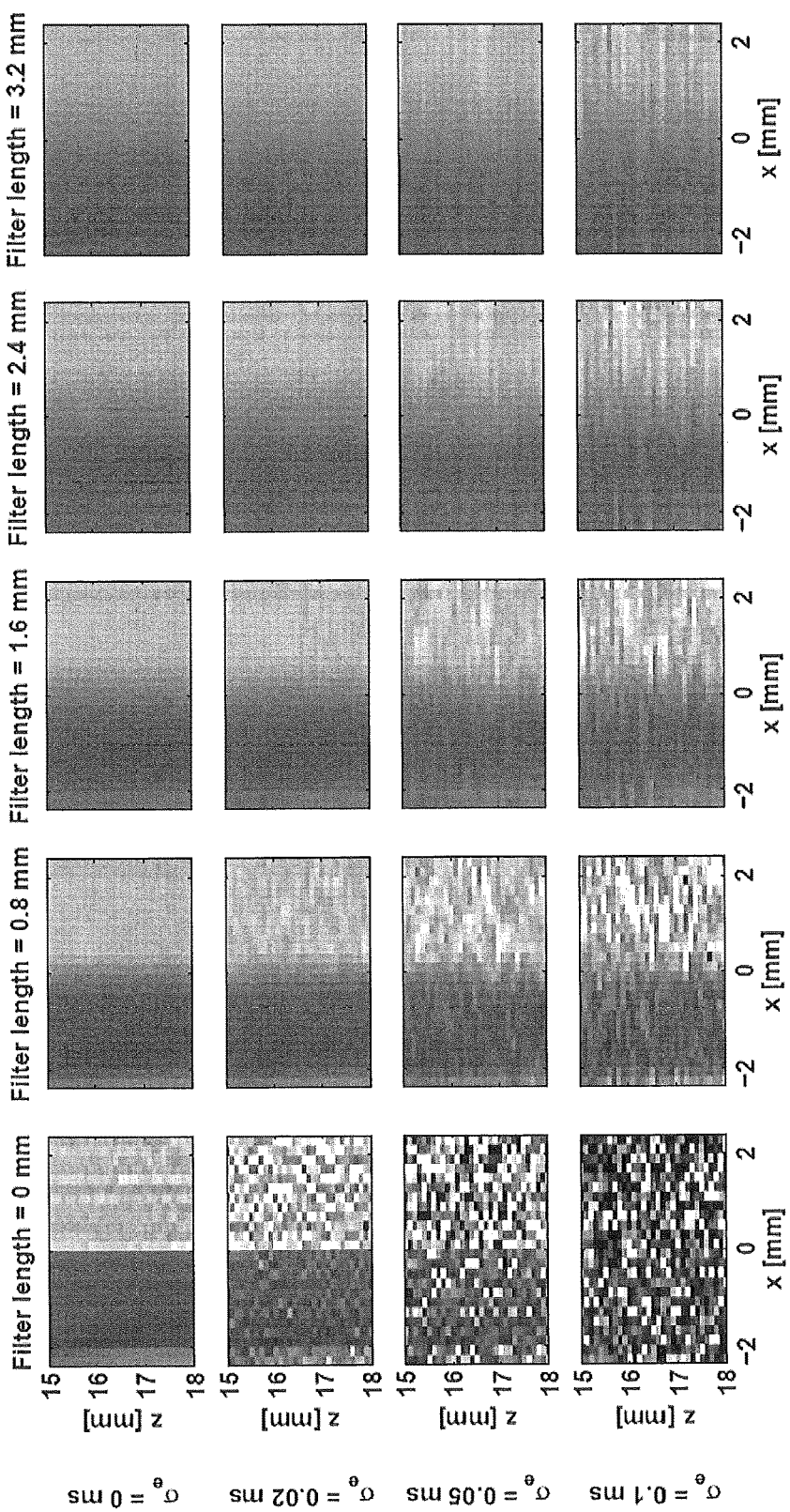
FIG. 8 is a series of shear wave images of a simulated phantom using moving linear regression kernels on the high resolution arrival time differences.

FIG. 8 illustrates shear wave images of a simulated phantom using a moving linear regression of progressively-estimated arrival times to reduce the effect of noise. Each row shows an increasing amount of jitter on the arrival time estimates, and each column shows an increasing filter size. In the presence of noise, the boundary becomes clearer as the filter increases; however, the edge resolution becomes worse.

Figure 9:
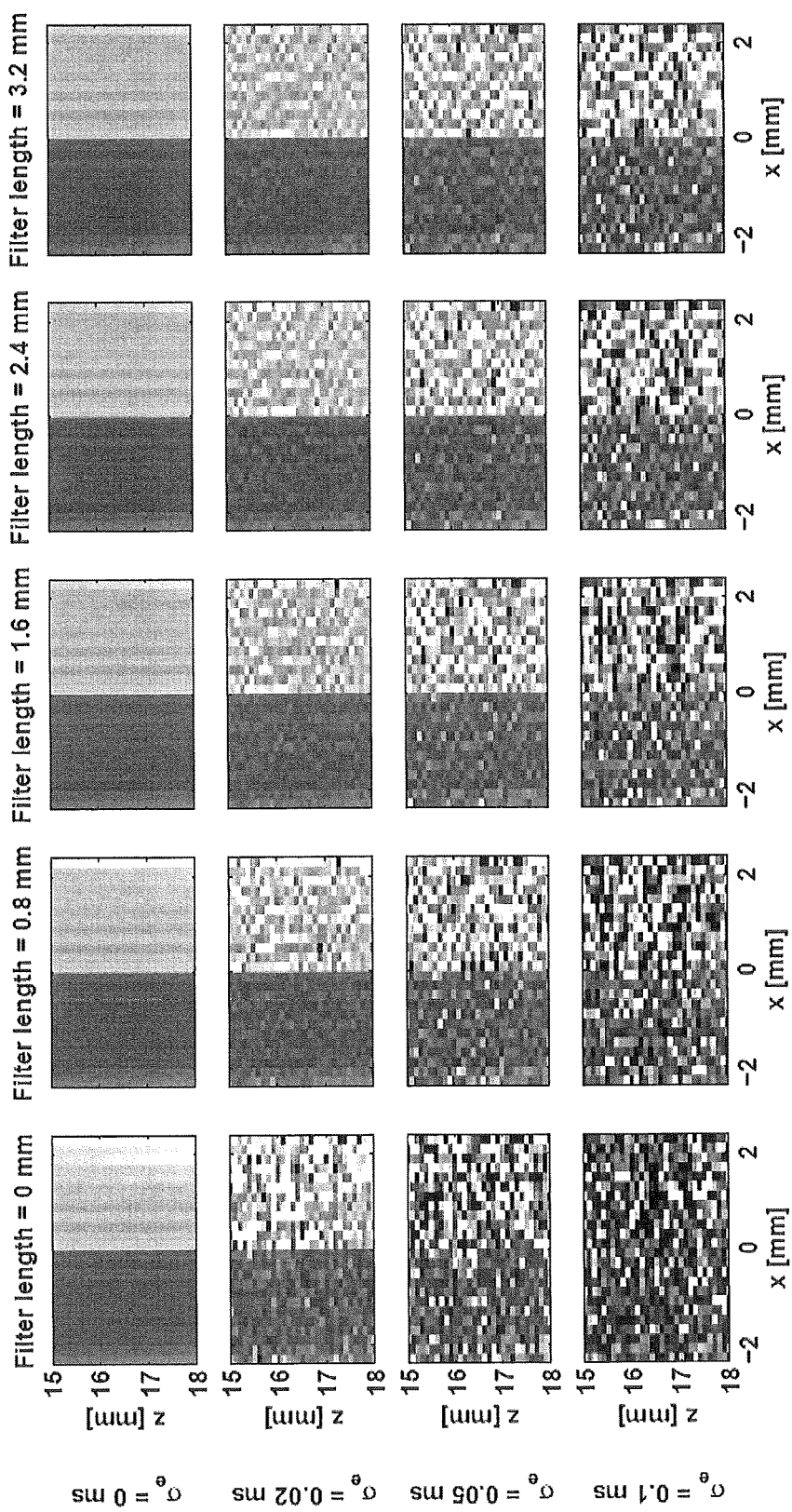
FIG. 9 is a series of shear wave images of a simulated phantom using multi-resolution kernels of increasing size according to some embodiments in which noise is reduced for larger kernels while maintaining edge resolution.

FIG. 9 illustrates shear wave images using the multi-resolution filter, which combines all combinations of arrival time differences within the filter kernel as described herein. Noise is reduced as the filter size is increased; however, no loss of resolution is observed.

Figure 10:
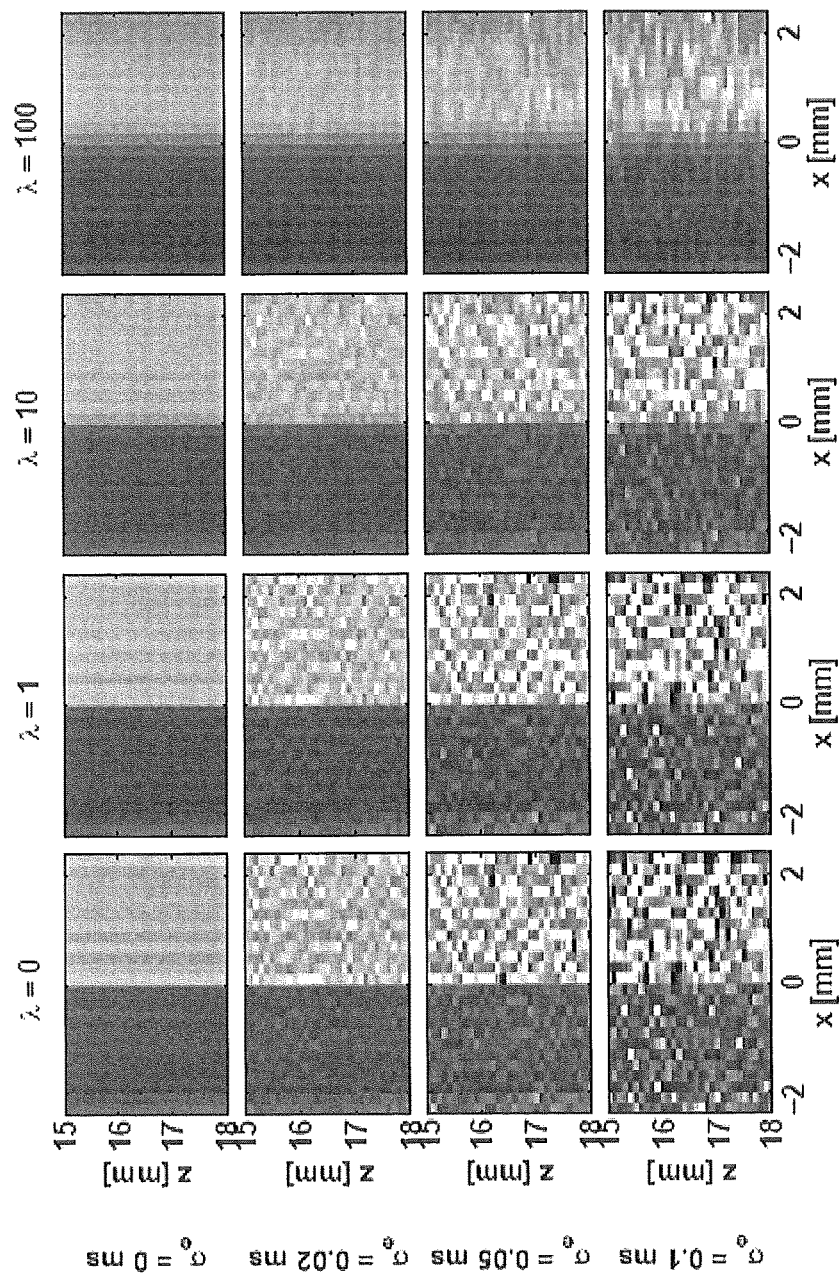
FIG. 10 is a series of shear wave images for the simulated phantom using a 1.6 mm multi-resolution kernel for different levels of noise and regularization according to some embodiments.

FIG. 10 illustrates the effect of regularization for a 1.6 mm multi-resolution kernel. By increasing the regularization scaling, $\lambda$, the noise is reduced more effectively than the linear regression shown in FIG. 8 while the edge resolution is decreased less.

Figure 11:
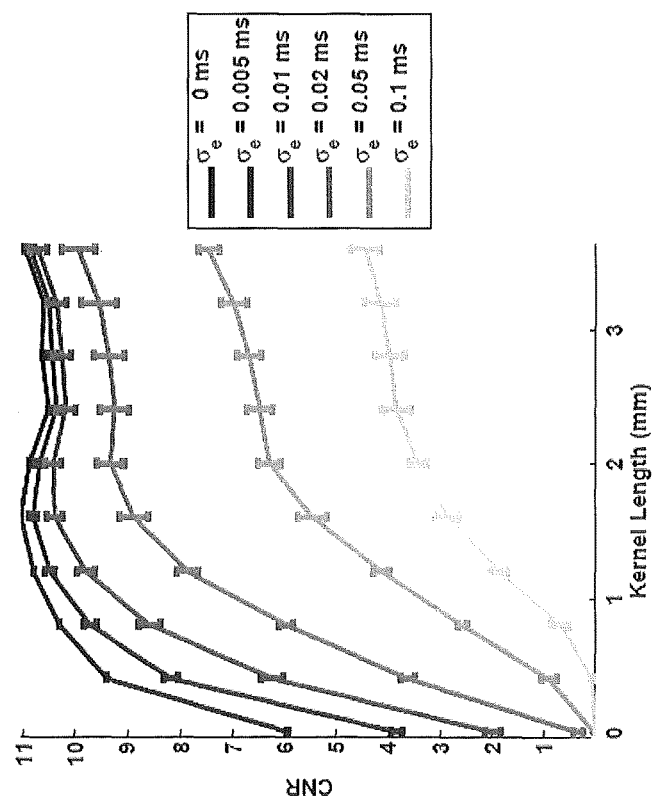
FIG. 11 is a graph of the Contrast-to Noise (CNR) as a function of kernel length of a moving linear regression filter of arrival times according to some embodiments.

FIG. 11 illustrates the Contrast-to-Noise (CNR) as a function of kernel length for a moving linear regression filter of arrival times at different noise levels. Error bars represent the standard deviation over 16 noise realizations. As noise increases, larger kernels may be needed to maintain CNR at acceptable levels.

Figure 12:
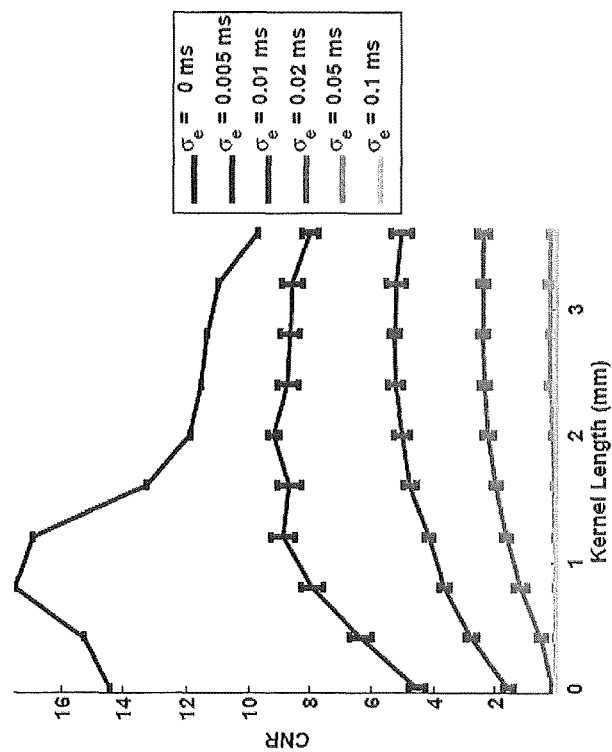
FIG. 12 is a graph of CNR as a function of multi-resolution filter size for different levels of noise according to some embodiments.

FIG. 12 illustrates CNR as a function of multi-resolution filter size for different levels of noise, with error bars representing variation over 16 noise realizations. The CNR values are similar to or lower than the equivalent points in FIG. 11 and level out for sizes of about 2 mm.

Figure 14:
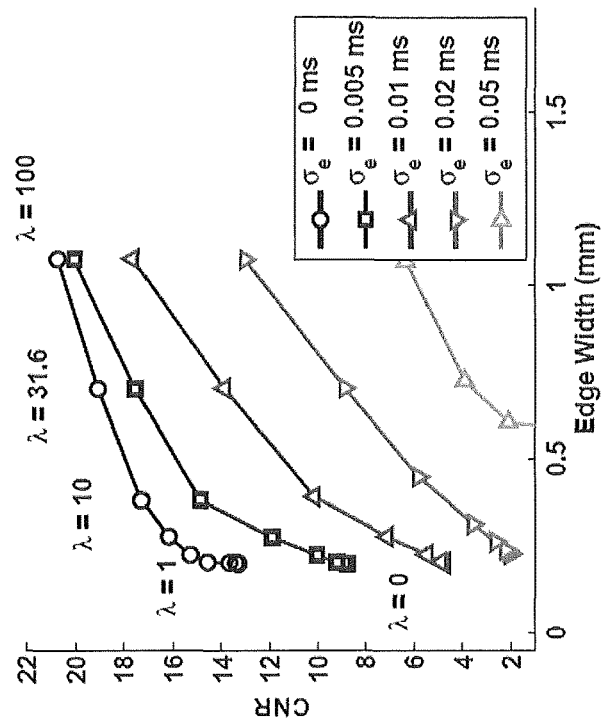
FIG. 14 is a graph of CNR-Resolution regularization tradeoff curves for a 1.6 mm multi-resolution kernel according to some embodiments. The lower left point of each curve (highest resolution, lowest CNR) is $\lambda=0$, and the upper right point (worst resolution, best CNR) is $\lambda=100$.
Figure 13:
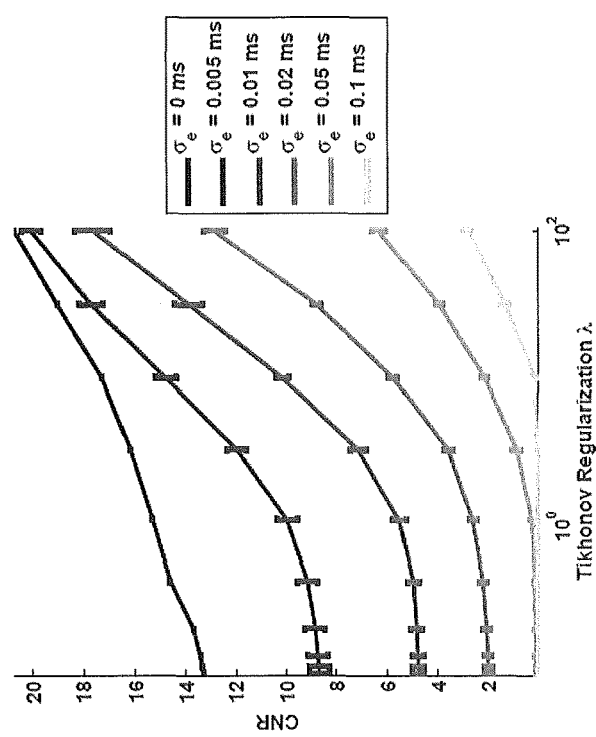
FIG. 13 is a graph of CNR as a function of Tikhonov regularization $\lambda$ for multiple noise levels using a 1.6 multi-resolution kernel in which $\lambda$ is shown on a logarithmic scale according to some embodiments.

The effect of regularization on CNR estimates from FIG. 12 is shown in FIG. 13. Increasing the scaling of the Tikhonov regularization term, $\lambda$, may cause significant increases in CNR that surpass the linear regression CNR values from FIG. 11. To illustrate how the increase in CNR afforded by regularization is accompanied by a corresponding decrease in edge resolution, FIG. 14 illustrates the matched CNR and resolution (100% edge width) values for each value of $\lambda$, and at each noise level. Increasing $\lambda$ increases CNR, but correspondingly decreases edge resolution.

Figure 15:
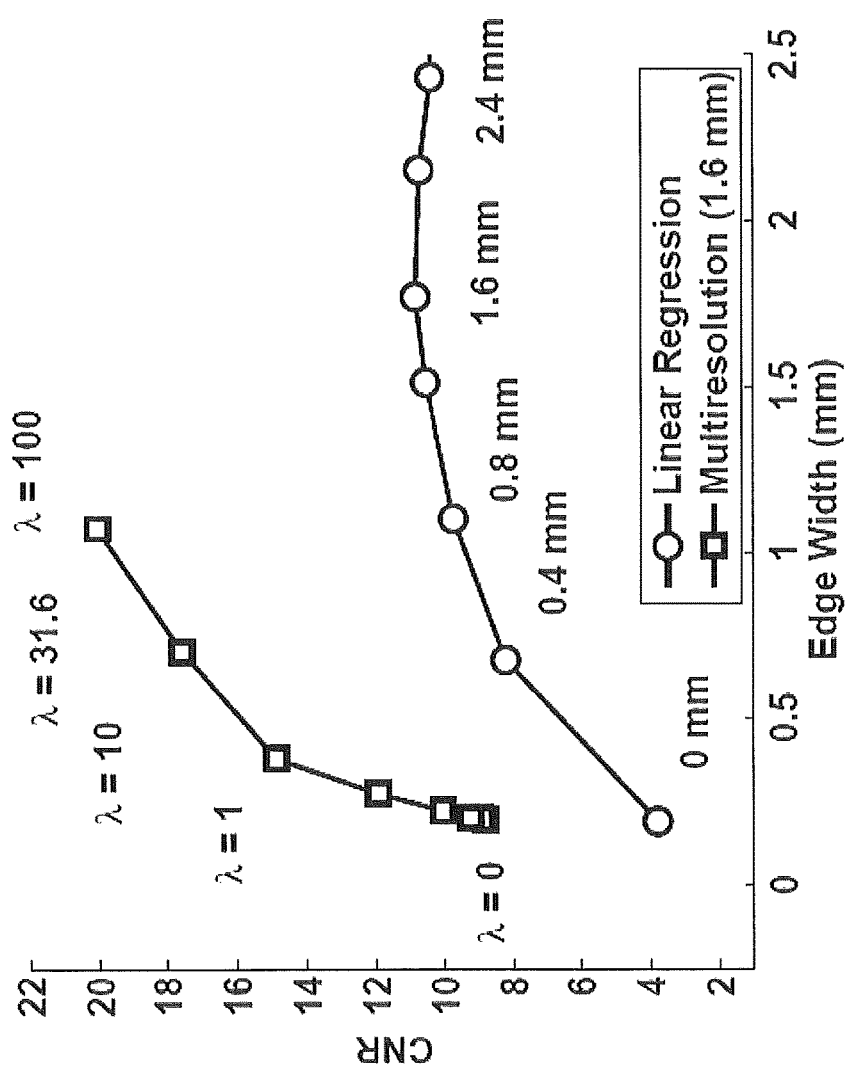
FIG. 15 is a graph of the CNR-Resolution tradeoff curves for multi-resolution (circles) and linear regression (squares) at the $\sigma_3=0.005$ ms noise level. The multi-resolution curve uses a 1.6 mm kernel and varies the regularization term $\lambda$, while the linear regression directly varies the filter size.

To compare the tradeoff of CNR and resolution in the multi-resolution techniques against the same tradeoff for linear regression, FIG. 15 illustrates both tradeoff curves, using a kernel of 1.6 mm and varying $\lambda$, for the multi-resolution scheme, and varying kernel length for linear regression. The noise level was set to 0.005 ms. With no regularization ($\lambda=0$), multi-resolution filtering has slightly lower CNR than linear regression using a 1.6 mm kernel, but for any given CNR value achieved by linear regression, the multi-resolution scheme can achieve the same CNR through regularization with significantly better resolution.

Although embodiments according to the invention are described herein with respect to solving the above system of equations by a Least-Squares solution, it should be understood that any suitable technique may be used. For example, a Maximum A Posteriori (MAP) estimation or any suitable inverse problem technique may be used. The above system of equations may be solved for sets of single values for time-of-flight pairs, such as the peak of the correlation function, or for sets of probability distributions functions (PDF's), including means and standard deviations, instead of for single values.

The foregoing is illustrative of the present invention and is not to be construed as limiting thereof. Although a few example embodiments of this invention have been described, those skilled in the art will readily appreciate that many modifications are possible in the example embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method for determining a mechanical parameter for a sample having a target region, the method comprising:
generating a displacement of the sample in the target region;
transmitting tracking pulses in the target region from an ultrasound transducer array having a plurality of transducer elements at a corresponding plurality of positions along the ultrasound transducer array;
receiving at the plurality of transducer elements of the ultrasound transducer array corresponding echo signals for the tracking pulses in the target region at the plurality of positions or acquisition times corresponding to the plurality of transducer elements;
selecting one or more spatially-related multi-resolution pairs of the plurality of positions and acquisition times;
analyzing the echo signals at one or more multi-resolution pairs of the positions or acquisition times;
wherein the spatially-related pairs of positions or acquisition times comprise a first set of positions of the plurality of positions corresponding to a first set of the plurality of transducer elements having a first resolution therebetween and a second set of positions of the plurality of positions corresponding to a second set of the plurality of transducer elements having a second resolution therebetween that is different from the first resolution,
the first and second sets of positions are spatially equivalent such that a sum of distances for the first set of positions of the first set of the plurality of transducer elements interrogates only a same overlapping area of the target region as a sum of distances for the second set of positions of the second set of the plurality of transducer elements;
determining at least one mechanical parameter of the target region based on the echo signals at the one or more multi-resolution pairs of positions or acquisition times that are spatially equivalent such that a sum of distances for the first set of positions of the first set of the plurality of transducer elements interrogates only a same overlapping area of the target region as a sum of distances for the second set of positions of the second set of the plurality of transducer elements; and
generating an image of the target region based on the at least one mechanical parameter.

2. The method of claim 1, wherein analyzing echo signals at one or more multi-resolution pairs of positions or acquisition times comprises determining a value from the group consisting of a time-of-flight and velocity of a shear wave.

3. The method of claim 2, further comprising averaging a value from the group consisting of a time-of-flight difference and a velocity estimate of the shear wave for the first and second sets of spatially equivalent positions.

4. The method of claim 1, wherein the plurality of positions comprise positions of ultrasound array elements that transmit the tracking pulses and receive the echo signals and positions of ultrasound array elements that transmit an excitation pulse configured to cause the tissue displacement.

5. The method of claim 1, wherein analyzing echo signals at one or more multi-resolution pairs of the positions or acquisition times comprises combining echo signals at the one or more multi-resolution pairs of positions.

6. The method of claim 1, wherein the at least one mechanical parameter from the group consisting of shear elasticity modulus, Young's modulus, dynamic shear viscosity, shear wave velocity and mechanical impedance of the target region.

7. The method of claim 1, wherein the target region comprises an in vivo human tissue sample.

8. The method of claim 1, wherein the displacement of the sample is detected with an internally inserted ultrasound probe array.

9. The method of claim 1, wherein the displacement of the sample is detected with an externally applied ultrasound array.

10. The method of claim 1, wherein the displacement of the sample comprises a shear wave that is generated with an applied shear wave source comprising selected from the group consisting of an ultrasound transducer and a mechanical vibrator.

11. The method of claim 1, wherein the displacement of the sample comprises an axial displacement of the sample.

12. An ultrasound system for determining a mechanical parameter for a target region, the system comprising:
an ultrasound transducer array having a plurality of transducer elements at a corresponding plurality of positions along the ultrasound transducer array;
a controller configured to control the ultrasound transducer to generate a tissue displacement in the target region, to transmit tracking pulses in the target region, and to receive corresponding echo signals for the tracking pulses in the target region at the plurality of positions corresponding to the plurality of transducer elements;
wherein the controller is further configured to receive signals from the ultrasound array, select one or more spatially-related multi-resolution pairs of positions or acquisition times, and analyze the echo signals at one or more multi-resolution pairs of positions or acquisition times,
wherein the spatially-related pairs of positions or acquisition times comprise a first set of positions of the plurality of positions corresponding to a first set of the plurality of transducer elements having a first resolution therebetween and a second set of positions of the plurality of positions corresponding to a second set of the plurality of transducer elements having a second resolution therebetween that is different from the first resolution,
the first and second sets of positions are spatially equivalent such that a sum of distances for the first set of positions of the first set of the plurality of transducer elements interrogates only a same overlapping area of the target region as a sum of distances for the second set of positions of the second set of the plurality of transducer elements;
wherein the controller is further configured to determine at least one mechanical parameter of the target region based on the echo signals at the one or more multi-resolution pairs of positions or acquisition times that are spatially equivalent such that a sum of distances for the first set of positions of the first set of the plurality of transducer elements interrogates only a same overlapping area of the target region as a sum of distances for the second set of positions of the second set of the plurality of transducer elements, and to generate an image of the target region based on the at least one mechanical parameter.

13. The system of claim 12, wherein controller is configured to analyze echo signals at one or more multi-resolution pairs of positions by determining a value selected from the group consisting of a time-of-flight and a velocity of a shear wave.

14. The system of claim 12, wherein the controller is further configured to average a value from the group consisting of a time-of-flight difference and a velocity estimate of the shear wave for the first and second sets of spatially equivalent positions.

* * * * *